United States Patent [19]
Duthoit et al.

[11] Patent Number: 4,828,565
[45] Date of Patent: May 9, 1989

[54] COTYLOIDAL COMPONENT FOR A NON-CEMENTED HIP PROSTHESIS

[76] Inventors: Etienne Duthoit, 8 allée des Hêtres, 59830 Cysoing; Jean-Alain Epinette, 27 rue Lamandin, 62700 Bruay-En-Artois; Yves Carlier, 13 rue Pierre Lhermitte, 80000 Amiens, all of France

[21] Appl. No.: 922,345

[22] Filed: Oct. 23, 1986

[30] Foreign Application Priority Data

Oct. 25, 1985 [FR] France .................. 85 15844

[51] Int. Cl.⁴ .................................. A61F 2/34
[52] U.S. Cl. .................................. 623/22; 623/18
[58] Field of Search ......................... 623/16–23

[56] References Cited

U.S. PATENT DOCUMENTS 3,608,096 9/1971 Link .......................... 623/22
3,840,904 10/1974 Tronzo ...................... 623/22

FOREIGN PATENT DOCUMENTS 0091315 10/1983 European Pat. Off. ....... 623/22
0121002 10/1984 European Pat. Off. ....... 623/22
2349357 4/1975 Fed. Rep. of Germany ... 623/22
2822585 3/1980 Fed. Rep. of Germany ... 623/22
2225924 11/1974 France ....................... 623/22
2416004 8/1979 France ....................... 623/22

Primary Examiner—Richard J. Apley
Assistant Examiner—David J. Isabella
Attorney, Agent, or Firm—Perry Carvellas

[57] ABSTRACT

A cotyloidal component for a non-cemented hip prosthesis comprises a hemispherical titanium dome member and a cup of polymer material which is engaged therein to form a friction lining and to receive the spherical head of a femoral component. The titanium dome member comprises a first zone in the form of a portion of a sphere which is angularly displaced with respect to the dome member to be tangential to the equatorial edge and to bear against the roof part of the acetabulum. Disposed in projecting relationship in the zone are two stud portions for the passage therethrough of screws provided to engage into the roof part of the acetabulum and form a primary anchoring means. The zone is covered with a covering of porous titanium capable of being invaded by growing spongy bone to form a secondary anchoring. The second zone is smooth and comprises slots along meridians of the dome member to afford a capacity for elastic deformation comparable to that of the acetabulum in the region of the horns thereof.

20 Claims, 2 Drawing Sheets

COTYLOIDAL COMPONENT FOR A NON-CEMENTED HIP PROSTHESIS

BACKGROUND OF THE INVENTION

1. Field of the Invention

The invention relates to hip prostheses and more particularly to a cotyloidal component of a hip prosthesis which is intended to be implanted without cement and which comprises a metal dome member to be fixed in a suitably prepared cotyloid cavity with a polar axis oriented substantially in the mean direction of the neck of the femur, and a cup of polymer material which is to be precisely fitted into the dome member to form a rubbing or friction lining and is to receive the spherical head of a femoral component so as to reproduce the natural joint.

2. Description of the Prior Art

The practice at one time was to fix the femoral and cotyloidal prosthesis components respectively in the femur and in the acetabulum of the iliac bone, by means of a polymerisable cement generally of the acrylic type.

That process suffered from a number of disadvantages with in particular the creation in the bones involved of lines of forces which were oriented in directions which were not natural ones, giving rise to pains, and the loss of plasticity of the sealing material in the course of time, with the result that clearance was formed between the bone and the corresponding component.

Hip prosthesis components were then produced, which were suitable for being implanted without cement, anchoring of such components in the bones which receive them being effected by strong mechanical connections.

The cotylidal components to which the present invention relates fall into three categories, in the present state of the art.

In a first category, the component comprises a metal dome or cap member of annular shape, provided with a peripheral outside screwthread which is to be engaged in a complementary thread provided in the wall of the acetabulum. The screwthreads are frequently self-tapping, with interrupted screwthread portions having cutting edges.

Positioning of the component in a prestressed condition is intended to ensure that the screwing effect is irreversible. However, osteolysis of the acetabulum sometimes occurs, resulting in the component suffering from play. In addition, the path of the lines of force from the femur to the iliac bone is somewhat different from that which occurs in the natural healthy joint, with an inclination with respect to the directions of greatest natural strength of the bone structure.

In a second category the component comprises a substantially hemispherical dome member or cap whose outside surface is provided with a covering of porous metal. That type of component, which originally was provided to improve the connection between the component and a cement, has been found to be suitable for promoting a direct connection between the metal component and the growing spongy bone which penetrates into the pores in the metal.

In fact, the connecting mechanism involving growth of the spongy bone which penetrates into the pores of the metal, commonly referred to as 'rehabilitation' is effective only after a period of time which is reckoned in weeks. Use is therefore made of a primary and immediate anchoring action which is achieved by means of screws which pass through passages in the dome member or cap and which are engaged into screwthreaded holes provided in the wall of the acetabulum. However the primary anchoring effect is relatively fragile, particularly when the patient suffers from bone ageing.

The first two categories of cotyloidal components suffer from the serious disadvantage of not complying with one of the basic points of mechanics insofar as deformations of the acetabulum which is subjected to tensile and compression stresses in response to the load of the hip are not followed with a sufficient degree of exactitude by the metal dome members.

A third category of cotyloidal components has been used, wherein those components are reduced to a dome member which generally speaking is of a substantially hemispherical outside shape and which is made of a polymer material having a level of elasticity close to that of the bone. More precisely, the flexibility of the polymer permits it to follow the resilient flexural movements of the bone in which it is housed. Primary anchoring is effected by means of one or more studs or pegs which are engaged into housings provided in the acetabulum.

In spite of having mechanical characteristics which are very close to those of the natural bone, that category of component is often considered to suffer from disadvantages, namely the absence of secondary anchoring by the formation of a fibrous interface between the bone and the polymer, and bleeding-out phenomena in respect of the polymer (plasticising agents) in direct contact with the tissues, which give rise to serious problems in regard to biocompatibility.

It is among the objects of the present invention to provide a cotyloidal component derived from the second category set forth above, which exhibits the following criteria:

conformity with the distribution of the natural lines of force in a healthy joint and the adjacent bones;

primary fixing of the component in the bone, in a strong and secure manner; and precise contact with the bone which, in conjunction with biomechanical properties which are close to those of the bone, permits an excellent secondary anchoring effect by boney rehabitation.

SUMMARY OF THE INVENTION

According to the invention there is provided a cotyloidal component of a hip prosthesis to be implanted without cement, wherein said cotyloidal component comprises a metal dome member which is generally hemispherical with an equatorial edge, has a polar axis and is to be fixed in a suitably prepared cotyloid cavity in the iliac bone with the polar axis oriented so as to be substantially in the mean direction of the neck of a femur which is to co-operate with the cotyloidal component, and a cup of polymer material to be engaged precisely in the dome member to form a rubbing lining therein and to receive a spherical head of the femur so as to reproduce the natural joint, wherein the dome member has on its outside surface a first zone which occupies a portion of a sphere and is covered with a covering of porous metal capable of being invaded by growing spongy bone, and a second zone which is generally smooth, the first zone having a polar axis which is angularly displaced with respect to the polar axis of the dome member so as to be oriented substantially in the natural direction of transmission of force from the femur to the iliac bone and including passages for anchoring means which penetrate into the wall of the cotyloid cavity, and the second zone having slots therein, the slots extending along meridians of the dome member from the equatorial edge thereof to the boundary with the first zone.

The first zone, in the form of a portion of a sphere, will be closely applied against the roof or top surface of the acetabulum, being centred on the mean axis of the natural lines of force, so that a secondary connection produced by 'rehabitation' of the covering of porous metal will essentially work in a compression mode. In addition, the slots in the second zone, jointly with the smooth surface thereof, impart to the component a degree of flexibility which will permit it to follow resilient deformation of the front and rear horns or spurs of the acetabulum.

It will be noted that the polar axes of the hemispherical dome member and the portion of a sphere which forms the first zone are necessarily convergent and intersect at the centre of the sphere generating the hemispherical dome member and the first zone. Because of the angle formed by those two polar axes, they define a plane which will be referred to as the common plane of the polar axes. A direct consequence of the angular displacement of the polar axes of the hemispherical dome member and the portion of the sphere forming the first zone is that the second zone which occupies the remainder of the hemisphere is variable in width, taken along the meridians of the dome member, the width of the second zone passing through the extrema in the common plane of the polar axes, that is to say being at a minimum in that plane on the same side as the polar axis of the portion of the sphere with respect to the polar axis of the dome member, and at a maximum on the opposite side. That means that the elasticity imparted to the dome member by the slots in the second zone will be at a maximum in the region of the horns or spurs of the acetabulum.

Moreover, preferably, the portion of the sphere forming the second zone has an edge tangential to the equatorial edge of the dome member, the minimum width of the second zone being zero, thus making it possible to impart a substantial degree of elasticity to the portion of the second zone which is to come to lie in the region of the horns or spurs of the acetabulum, while giving the first zone a sufficient surface area for connection to the roof or top surface of the acetabulum by a 'rehabitation' effect.

In a preferred arrangement, the passages for the anchoring means are two in number, being disposed symmetrically with respect to the common plane of the polar axes. That arrangement promotes correct positioning of the component and in particular suitable orientation of the polar axis of the part-spherical first zone.

Preferably the passages are provided on the axes of two cylindrical stud portions in projecting relationship on the outside face of the dome member, said axes being parallel to each other and parallel to the common plane of the polar axes. On the one hand those projecting portions are placed in suitably bored housings in the roof or top of the acetabulum, with a reduced amount of clearance, thus ensuring precise positioning of the component therein; on the other hand, the projecting portions form guides for screws forming anchoring means, the screws penetrating into the roof or top of the acetabulum at a position and with a precise orientation, which are determined so that the screws are disposed in a solid part of the iliac bone.

The outside surface of the projecting stud portions is preferably covered with porous metal to promote a secondary anchoring effect which resists any movement of the dome member with respect to the roof or top part of the acetabulum, with the spongy rehabitation bone essentially operating in a compression mode.

In a preferred arrangement, the dome member has a housing for the cup, with a bottom in the form of a concave portion of a sphere and connected to the equatorial edge by a frustoconical wall.

That arrangement, with a good support effect for the cup distributed over the bottom of its housing in the dome member, ensures that the polar axes of the dome member and the cup are coincident, by virtue of the frustoconical interengagement.

It will often be advantageous for the housing for the spherical head of the associated femoral component which is provided in the cup to embrace a spherical angle which is a little greater than a hemisphere, so that the spherical head of the femoral component can penetrate into its housing without excessive force but is positively held in that housing.

The above, and other objects, features and advantages of the invention will be apparent from the following detailed description of illustrative embodiments which is to be read in connection with the accompanying drawings.

DESCRIPTION OF THE PREFERRED EMBODIMENT

Figure 1:
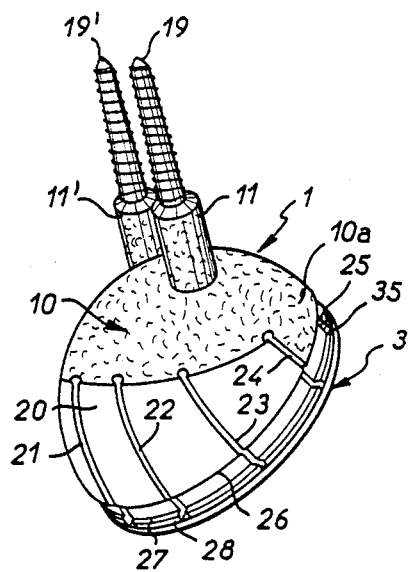
FIG. 1 is a perspective view of a cotyloidal component according to the invention.
Figure 2:
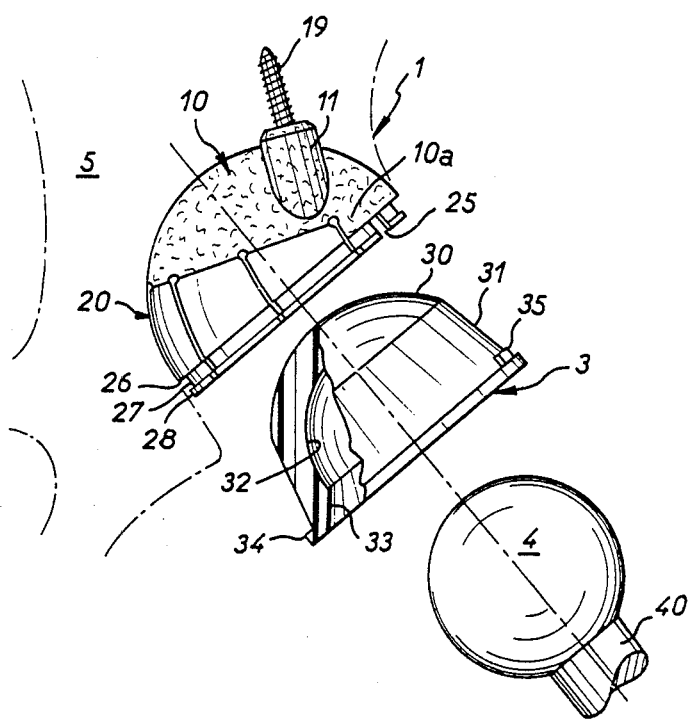
FIG. 2 is an exploded view of a hip prosthesis incorporating a component according to the invention.

In the selected embodiment as illustrated in FIGS. 1 through 5, the cotyloidal component conventionally comprises a metal dome member 1 which is fixed in the cotyloid cavity of the iliac bone 5, and a cup 3 of polymer material which fits precisely into the dome member 1 and which is capable of accommodating in a cavity 32 the spherical head 4 of a femoral component, the head 4 being fixed to the end of a neck 40. It will be noted that the dome member 1 and the cup 3 have polar axes 1b which are coincident with the mean direction of the axis of the neck 40.

The metal dome member 1 is preferably of titanium of generally hemispherical shape and has a first zone 10 in the general form of a portion of a sphere with a polar axis 10b which forms an angle A1 of about 30° with the polar axis 1b of the dome member 1. The portion 10 extends in a meridian plane over about 120° so that the circle defining the edge of the spherical portion 10 is tangential to the equatorial edge 26 of the dome member 1 at a point 26b, obviously in the plane which is common to the polar axes 1b and 10b.

The outside surface of the dome member 1 comprises a second zone 20 which is disposed between the spherical portion 10 and the equatorial edge 26 of the dome member 1. Machined in the second zone 20 are slots 21, 22, 22', 23, 23', 24 and 24' which extend over the entire width of the second zone 20 along meridians of the dome member 1. The longest slot 21 starts from a point 26a on the equatorial edge 26 which is disposed in the common plane of the polar axes 1b and 10b and diametrally opposite the point 26b where the spherical portion 10 is tangential with respect to the equatorial edge 26.

The slots 22 and 22', 23 and 23' and 24 and 24' are respectively symmetrical with respect to the common plane of the polar axes 1b and 10b. The end slots 24 and 24' are angularly spaced at 110° on the equatorial circle of the dome member 1 and, between those end slots 24 and 24', the slots 23, 22, 21, 22' and 23' are regularly spaced angularly along the equatorial circle of the dome member 1. The slots terminate at the edge of the spherical portion 10 in bores which are normal to the dome member, the bores being provided to reduce the concentration of stresses due to flexing of the lobes of the second zone 20.

The first zone 10 is extended beyond the spherical portion with its polar axis 10b, to the equatorial edge 26 of the dome member, between the end slots 24 and 24', by means of two curved-line triangles 10a and 10'a.

The dome member is also extended, beyond the equatorial edge 26, by a cylindrical ring portion comprising a groove 27 followed by a raised or bead portion 28 so as to permit gripping of the dome member when it is being set in position in the cotyloid cavity. The cylindrical ring portion comprises at least one notch or recess 25, the function of which will be specified hereinafter.

Disposed in the first zone 10 are two stud portions 11 and 11' which project outwardly. The projecting stud portions are cylindrical and have mutually parallel axes which are parallel also to the common plane of the polar axes 1b and 10b of the dome member 1 and the zone 10. The axes will be identified as 11b and 11'b; the axis 11'b is not shown, being coincident in FIG. 3 with the axis 11b. Moreover, hereinafter, the elements relating to the projecting stud portions 11 and 11' will be identified by a reference number, with a prime in relation to the projecting stud portion 11', even if the drawings show only one of those elements, by virtue of the symmetry of the arrangements involved.

The projecting stud portions 11 and 11' have bores 12 and 12' extending therethrough along their axes 11b and 11'b, in which screws 19 and 19' are guided (see FIGS. 1 and 2); those screws 19 and 19' form a primary anchoring for the dome member 1 in the cotyloid cavity, by being screwed into the roof or top part of the acetabulum. The upper edge of each stud portion 11 and 11' has a respective chamfer 11a and 11'a. Spot facings 12a and 12'a are provided at the base of the stud portions, in the inside wall of the dome member 1, for receiving the heads of the screws 19 and 19' therein.

The outside surface of the first zone 10 in the form of a portion of a sphere, including the curved-line triangles 10a and 10'a, the side faces and the terminal edges of the projections 11 and 11', has a covering of porous titanium produced by plasma torch spraying, which is intended to be invaded by the growing spongy bone to form secondary anchoring for the cotyloidal component.

Figure 3:
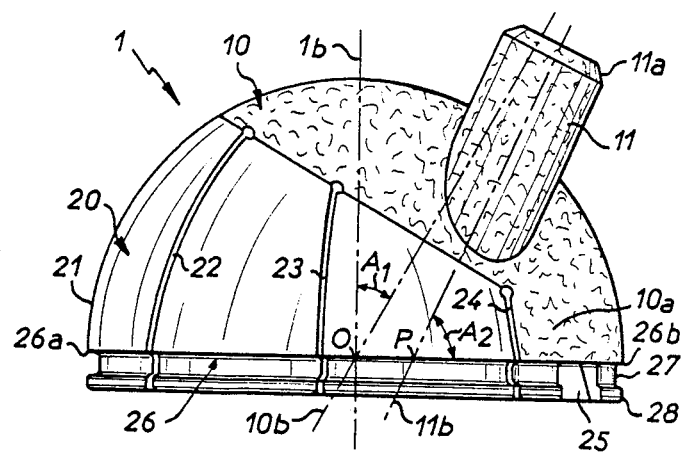
FIG. 3 is a view in side elevation of a cotyloidal component.
Figure 4:
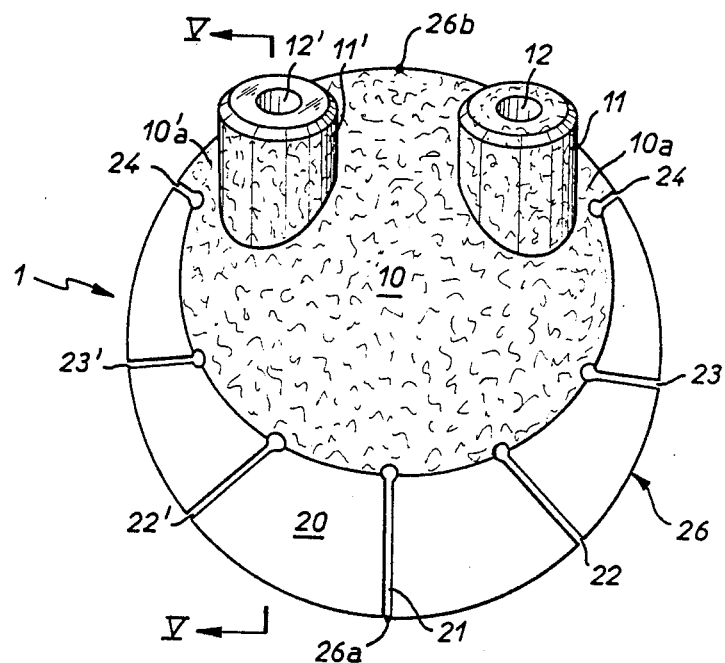
FIG. 4 is a plan view of the cotyloidal component shown in FIG. 3.
Figure 5:
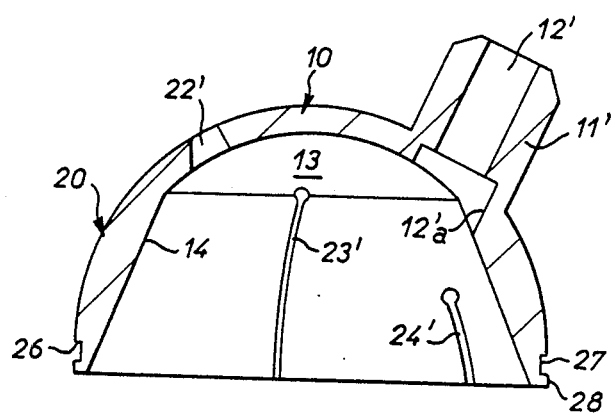
FIG. 5 is a view in section taken along line V—V in FIG. 4.

The axes 11b and 11'b of the stud portions 11 and 11' form a dihedral angle A2 which is between 60° and 70° and which is preferably 65°, with the equatorial plane of the dome member 1 where the equatorial edge 26 is located. The apex P of that dihedral angle, seen end-on in FIG. 3, is at a distance from the centre O of the equatorial edge 26 of the dome member 1, which is substantially equal to 2/9 of the radius of the hemisphere of the dome member.

Moreover, the stud portions 11 and 11' are substantially 10 mm in diameter and their axes 11b and 11'b are spaced at about 20 mm. All the dimensions indicated hereinbefore were arrived at in order for the paths of the lines of force between the femur and the iliac bone to be on average in conformity with the natural paths.

The internal shape of the dome member 1 is complementary to the external shape of the cup 3. It comprises a concave portion of a sphere 13 having the same centre as the dome member 1 and a frustoconical portion 14, with the axes thereof being coincident with the polar axis of the dome member 1. The cup 3 which is of biologically compatible polymer material correspondingly comprises on its outside a portion of a sphere 30 and a frustoconical portion 31. Co-operation as between the frustoconical portions 14 and 31 ensures coincidence in respect of the polar axes of the dome member 1 and the cup 3 while mutual contact as between the spherical portions 13 and 30 facilitates transmission of the forces involved.

Provided within the cup 3 is a substantially hemispherical cavity 32 corresponding to the spherical head 4 of the associated femoral component. It will be noted that the cavity 32 will advantageously extend over a little more than a hemisphere in order for engagement of the spherical head 4 therein to necessitate slight deformation of the opening of the cavity 32, and in order for the head 4 to be held in the cavity.

The edge of the cavity 32 is extended by a 45° chamfer 33 which facilitates the operation of introducing the head 4 into the cavity 32 and, by co-operating with the cylindrical neck 40 of the femoral component, forms a limit in regard to the pivotal movement of the prosthesis.

The frustoconical portion 31 of the cup 3 terminates with an annular rim portion 34 which comes into contact with the raised or bead portion 28 on the dome member 1 when the cup 3 is set in position, and makes it easier to handle the cup 3. Provided at the base of the frustoconical portion 31 and in projecting relationship on the rim portion 34 is at least one lug or stud 35 which engages in the notch or recess 25 in the ring portion 27, 28 of the dome member 1, and locks the cup 3 non-rotatably in the dome member 1.

For the operation of setting the prosthesis in place, although that operation per se is not within the scope of the present invention, the cotyloid cavity is prepared to be of hemisphere form of suitable diameter and the housings for the stud portions are produced by means of jigs, with an orientation such that the polar axis 1b of the dome member 1 is approximately at 40° in a plane perpendicular to the general axis of the trunk, with the meridian plane of the central slot 21 vertical (with respect to the patient when standing upright). The dome member 1 is set in position and the screws 19 and 19' are fully screwed into the roof or top part of the acetabulum. The cup 3 is then set in position and the joint can be remade by engaging into the internal cavity in the cup 3, the spherical head 4 of a femoral component which in the meantime will have been fitted into the femur.

It will be appreciated that the stud portions 11 and 11' resist any rotary movement of the dome member 1 in the cotyloid cavity, as from the stage of primary anchoring, with a higher degree of precision than when using screws alone. Thus, invasion of the covering of porous titanium by the growing spongy bone will not be retarded or interfered with by minor movements of the dome member with respect to the acetabulum when the joint functions.

Moreover, welding of the dome member 1 to the iliac bone 5 by 'rehabitation' occurs in the first zone corresponding to the roof or top part of the acetabulum where bony flexural movements are very slight, while the second zone 20 is still capable of small movements with respect to the bone against which it bears, so that the elasticity of the second zone, due to the slots, can accompany the flexural movements of the bone, which become increasingly substantial with decreasing distance from the front and rear horns or spurs of the acetabulum. The latitude of elastic deformation of the second zone 20 does in fact increase with the width of that zone.

It will be appreciated that the invention is not limited to the embodiments described, in particular when the description refers to numerical values, but embraces all the alternative forms thereof, which fall within the scope of the claims.

What is claimed is:

1. A cotyloidal component of a hip prosthesis to be implanted without cement, wherein the cotyloidal component comprises a metal dome member having a generally hemispherical outer surface, an equatorial edge lying in an equatorial plane and a dome polar axis perpendicular to the equatorial plane, the cotyloidal component being adapted to be fixed in a prepared cotyloidal cavity in an iliac bone with the dome polar axis directed substantially towards the neck of an associated femur, and a cup of polymer material to be fitted precisely in the dome member to form a lining therein and to receive a spherical head of the femur so as to define a joint, the dome member having on its hemispherical outside surface a first zone which extends over a first portion of the dome surface and is covered with a porous metal capable of being invaded by growing spongy bone, the surface area of said first zone being sufficient to form secondary anchoring means for said cotyloidal component, and a second zone which extends over a second portion of the dome surface and which is generally smooth and non-porous, the first and second zones forming a boundary therebetween, the first zone having a first zonal polar axis which intersects the dome polar axis at the center of the dome member equatorial plane and forms an angle of about 30° with the dome polar axis, the first zonal polar axis and the dome polar axis forming a common plane, the first zonal polar axis being directed substantially in the natural direction of transmission of force from the femur to the iliac bone, the first zone including passages for anchoring means which are adapted to penetrate into the wall of the cotyloidal cavity, and the second zone having slots therein, the slots extending along meridians of the dome member from the equatorial edge of the dome member to the boundary between the first zone and the second zone.

2. The cotyloidal component of claim 1, wherein the first zone is in the general form of a portion of a sphere having an outer edge tangential to the equatorial edge of the dome member at a point opposite to the second zone.

3. The cotyloidal component of claim 1, wherein the slots are odd in number and comprise a central slot lying in the common plane formed by the dome polar axis and the first zonal polar axis and the other slots are dispersed symmetrically in pairs with respect to said common plane.

4. The cotyloidal component of claim 1, wherein there are two slots spaced an equal distance away from and opposite to the central slot and are spaced from each other at an angle of approximately 110° along the equatorial edge of the dome member and the first zone extends between said end slots and the equatorial edge of the dome member.

5. The cotyloidal component of claim 3, wherein there are seven regularly spaced slots.

6. The cotyloidal component of claim 1, wherein the passages for the anchoring means comprise two passages disposed symmetrically with respect to the common plane formed by the dome polar axis and the first zonal polar axis.

7. The cotyloidal component of claim 6, wherein said passages comprise cylindrical stud portions each having a central axis, the stud portions projecting outwardly from the outside surface of the dome member, the passages being along the axis of each of the cylindrical stud portions and said axes being parallel to each other and symmetrical with respect to the common plane formed by the dome polar axis and the front zonal polar axis.

8. The cotyloidal component of claim 7, wherein the two parallel axes of the stud portions form a plane, which plane forms a dihedral angle with a plane formed by the equatorial edge of the dome member which angle is between 60° and 70°.

9. The cotyloidal component of claim 8, wherein the dihedral angle has an apex spaced from a center of a circle formed by the equatorial edge of the dome member at a distance equal to about 2/9th of the radius of said circle.

10. The cotyloidal component of claim 7, wherein the stud portions have an outside surface, the outside surface of the stud portions having a covering of porous metal.

11. The cotyloidal component of claim 1, wherein the equatorial edge has a ring extension portion in which a generally radially outwardly opening groove is provided.

12. The cotyloidal component of claim 1, wherein the equatorial edge has a ring extension portion in which a generally outwardly opening groove is provided and wherein the ring extension portion has at least one notch engageable with a corresponding projection portion on the cup.

13. A cotyloidal component of claim 1, wherein the dome member has a cavity in which the cup is to be fitted precisely, the cavity having a spherical bottom surface and a frusto conical wall connecting the bottom surface to the equatorial edge of the dome member.

14. The cotyloidal component of claim 1, wherein the cup has a hemispherical shape cavity with an opening which accommodates the spherical head of the femoral component and the cup extends over more than a hemisphere, and the elasticity of the opening of the cup being sufficient to allow insertion of the spherical head.

15. The cotyloidal component of claim 1, wherein the length of the respective slot gradually increases from the circumferential ends of the second zone toward its middle.

16. The cotyloidal component of claim 1, wherein the first zonal polar axis intersects the hemispherical outer surface of the dome at the center of the porous metal covered surface of the first zone.

17. The cotyloidal component of claim 1, wherein the first zone is in the general form of a portion of a sphere having an outer circular edge.

18. The cotyloidal component of claim 1, wherein the first zone is in the general form of a portion of a sphere having an outer circular edge and a portion of the first zone outer circular edge is tangential to the equatorial edge of the dome member at a point within the common plane formed by the first zonal polar axis and the dome polar axis.

19. A cotyloidal component of a hip prosthesis to be implanted without cement, wherein the cotyloidal component comprises a metal dome member having a generally hemispherical outer surface, an equatorial edge lying in an equatorial plane and a dome polar axis perpendicular to the equatorial plane, the cotyloidal component being adapted to be fixed in a prepared cotyloidal cavity in an iliac bone with the dome polar axis directed substantially towards the neck of an associated femur, and a cup of polymer material to be fitted precisely in the dome member to form a lining therein and to receive a spherical head of the femur so as to define a joint, the dome member having on its hemispherical outside surface a first zone which extends over a first portion of the dome surface and is covered with a porous metal capable of being invaded by growing spongy bone, the surface area of said first zone being sufficient to form secondary anchoring means for said cotyloidal component, and a second zone which extends over a second portion of the dome surface and which is generally smooth and non-porous, the first and second zones forming a boundary therebetween, the first zone having a first zonal polar axis which intersects the dome polar axis at the center of the dome member equatorial plane and forms an angle of about 30° with the dome polar axis, the first zonal polar axis and the dome polar axis forming a common plane, the first zonal polar axis being directed substantially in the natural direction of transmission of force from the femur to the iliac bone, the first zone including passages for anchoring means which are adapted to penetrate into the wall of the cotyloidal cavity, and the second zone having slots therein, the slots extending along meridians of the dome member from the equatorial edge of the dome member to the boundary between the first zone and the second zone.

20. A cotyloidal component of a hip prosthesis to be implanted without cement, wherein the cotyloidal component comprises a metal dome member having a generally hemispherical outer surface, an equatorial edge lying in an equatorial plane and a dome polar axis perpendicular to the equatorial plane, the cotyloidal component being adapted to be fixed in a prepared cotyloidal cavity in an iliac bone with the dome polar axis directed substantially towards the neck of an associated femur, and a cup made of polymer material fitted precisely in the dome member to form a lining therein and to receive a spherical head of the femur so as to define a joint, the dome member having on its hemispherical outside surface a first zone in the general form of a portion of a sphere having an outer circular edge, said first zone extends over a first portion of the dome surface and is covered with a porous metal capable of being invaded by growing spongy bone, the surface area of said first zone being sufficient to form secondary anchoring means for said cotyloidal component, and a second zone which extends over a second portion of the dome surface and which is generally smooth and non-porous, the circular edge of the first zone forming a boundary between the first and second zones, the first zone having a first zonal polar axis which intersects the hemispherical outer surface of the dome at the center of the first zone and which intersects the dome polar axis at the center of the dome member equatorial plane and forms an angle of about 30° with the dome polar axis, the first zonal polar axis and the dome polar axis forming a common plane, the first zonal polar axis being directed substantially in the natural direction of transmission of force from the femur to the iliac bone, the first zone including passages for anchoring means which are adapted to penetrate into the wall of the cotyloidal cavity, and the second zone having slots therein, the slots extending along meridians of the dome member from the equatorial edge of the dome member to the boundary between the first zone and the second zone.

* * * * *